United States Patent [19]

Navarre, Jr.

[11] 4,094,187
[45] June 13, 1978

[54] STACK GAS ANALYZING SYSTEM WITH CALIBRATING/SAMPLING FEATURE

[75] Inventor: Anatole Joseph Navarre, Jr., Houston, Tex.

[73] Assignee: Champion International Corporation, Stamford, Conn.

[21] Appl. No.: 818,161

[22] Filed: Jul. 22, 1977

[51] Int. Cl.² .............................................. G01N 1/22
[52] U.S. Cl. .................................. 73/1 G; 73/421.5 A
[58] Field of Search ........................... 73/1 G, 421.5 R

[56] References Cited

U.S. PATENT DOCUMENTS

| 3,449,958 | 6/1969 | Bailey | 73/1 G |
| 3,924,442 | 12/1975 | Kerho | 73/1 G |

Primary Examiner—S. Clement Swisher
Attorney, Agent, or Firm—Evelyn M. Sommer

[57] ABSTRACT

A stack gas analyzer with a sampling probe mounted in the stack has a subsystem for supplying calibrating gases and blanking air to one or more gas analyzers either through the probe or directly. The rates of flow in the system are established to permit the analyzers to be flooded with calibrating gases or blanking air at any time without interrupting the operation of equipment which normally conveys stack gases to the analyzers.

23 Claims, 5 Drawing Figures

STACK GAS ANALYZING SYSTEM WITH CALIBRATING/SAMPLING FEATURE

BACKGROUND OF THE INVENTION

The present invention relates to fluid detecting systems and more particularly to a stack gas analyzer system having improved calibrating and sampling subsystems.

Effluent or exhaust gases from many industrial processes must be monitored and analyzed to be certain that concentrations of certain constituents do not exceed prescribed limits. While effluent flows can be monitored by capturing an effluent sample in a sealable container and by transporting that container to one or more analyzers in a laboratory environment, more sophisticated effluent analyzers include conduits or pipes for conveying effluent directly to one or more nearby analyzers. Such fluid analyzers provide a "real-time" analysis of the effluent flow to permit the process parameters to be adjusted without delay, thereby reducing the chances that unacceptable levels of pollutants will be exhausted to the atmosphere.

The analyzers of such "real-time" systems must, of course, be calibrated periodically to ensure that the system accuracy remains at acceptable levels. In general, the systems are calibrated by supplying known concentrations of suspected effluent constituents to the analyzers to determine whether the analyzer reading corresponds to the known concentration.

One problem with known calibration systems is that the calibrating fluids are normally supplied directly to the analyzers and do not enter the analyzers through the path followed by effluent samples. Any part of a sample system can react with one or more constituents in effluent flow, causing the analyzers to read post-reaction concentrations which may not match concentrations in the main effluent flow. since the effect of sample system reactions with traversing effluent fluids is not easily determined, calibration errors in such systems are not easily eliminated.

Another problem which occurs during the use of prior calibration systems is that the calibrating operations are not necessarily performed under conditions which exist during normal effluent sampling operations. Variations in flow rates and pressures can be significant as these may affect the concentrations of constituents which ultimately reach the analyzers during calibrating or effluent sampling operations.

Still another problem which exists in prior art analyzers is that the sample supply has normally been insufficient to drive more than one or very few analyzers. Where several different analyzers were needed to detect the presence of different constitutents in the effluent, a number of sampling systems have had to be provided. This, of course, adds to the expense of installing and maintaining the entire analyzer system.

SUMMARY OF THE INVENTION

The present invention is an effluent analyzing system to be used with one or more analyzers for detecting the presence of suspected constitutents in an effluent flow. A calibration/sampling system is included which permits the analyzers to be calibrated by means of calibrating fluid which follows the same path to the analyzers as is followed by effluent samples. The calibration/sampling system also permits the calibrating and sampling operations to be carried out at substantially the same conditions of flow rates and pressures as exist during effluent sampling.

A system constructed in accordance with the present invention includes a chambered probe which has a first inlet for receiving samples of effluent, a second inlet and an outlet. The probe outlet leads to a sample delivery means which transfers the contents of the probe to the analyzers at a predetermined rate of flow. A calibrating fluid supply is connected to the second inlet of the probe. This fluid supply can selectively supply known concentrations of fluids at a rate of flow greater than the rate established by the sample delivery means. When the calibrating fluid supply does supply fluids to the probe, the effluent is forced from the chambered probe through the first inlet, thereby permitting the analyzers to be flooded with calibrating fluids delivered through the sample delivery means to the exclusion of effluent fluid samples.

DESCRIPTION OF THE DRAWINGS

While the specification concludes with claims particularly pointing out and distinctly claiming that which is regarded as the present invention, details of preferred embodiments of the invention may be more readily ascertained from the following detailed description when read in conjunction with the accompanying drawings wherein:

DESCRIPTION OF PREFERRED EMBODIMENTS

Figure 1:
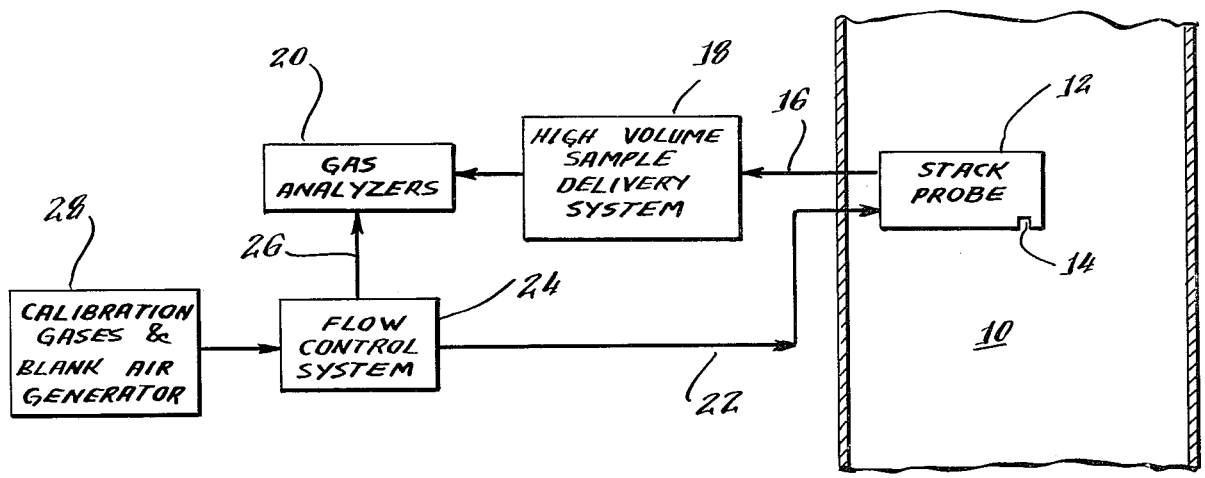
FIG. 1 is a basic block diagram of an analyzer system incorporating the present invention.

Referring to FIG. 1, a preferred application of the present invention is as a stack gas analyzer system for detecting the presence of potential atmospheric pollutants in a stack 10. Examples of such pollutants include hydrogen sulfide and sulfur dioxide. A stack probe 12, the construction of which will be described in detail later, is mounted within stack 10 to receive stack gas at a first inlet 14. The probe 12 includes an outlet 16 to a high volume sample delivery system 18 which transfers the contents of the probe to one or more gas analyzers 20. Each of the analyzers 20 measures the concentration of one or more potential pollutants. The probe 12 has a second inlet 22 from a flow control system 24, which also includes a direct connection 26 to the gas analyzers 20. The system also includes a calibration gases and blank air generator 28 for supplying both known concentrations of suspected stack gas constitutents and blanking air to the flow control system 24. The flow control system 24 can direct the calibrating gases and blank air directly to the gas analyzers 20 through connection 26 or, in the alternative, through connection 22 to the stack probe 12.

As will be described in more detail below, the rate at which the calibrating gases or blanking air is supplied to the stack probe exceeds the rate at which the high volume sample delivery system can deliver samples to the gas analyzers. Therefore, when delivered to the probe 12 through connection 22, the calibrating gases flood the probe to force the stack gases back through inlet 14 to stack 10. The high volume delivery system transfers the calibrating gases from the interior of the probe 12 to the gas analyzers 20. Since the calibrating gases travel the same path as the stack gases during normal sampling operations, the sample system reacts with the calibrating gases in the same way it reacts with the stack gases. By calibrating the analyzers using calibrating gases delivered through probe 12, outlet 16 and high volume sample delivery system 18, any reactions within the sampling system are automatically compensated for.

The high volume sample delivery system 18 actually delivers more gas than can be accepted by the gas analyzers 20 with the excess being vented to the exterior of the system at a point between analyzers 20 and system 18. Preferably, the excess is returned to the stack 10 downstream of probe 12. Thus, system 18 establishes and maintains a fixed rate of flow and fixed pressure at the input to the gas analyzers whether the calibrating gases or stack gases are being drawn through the system.

Figure 2:
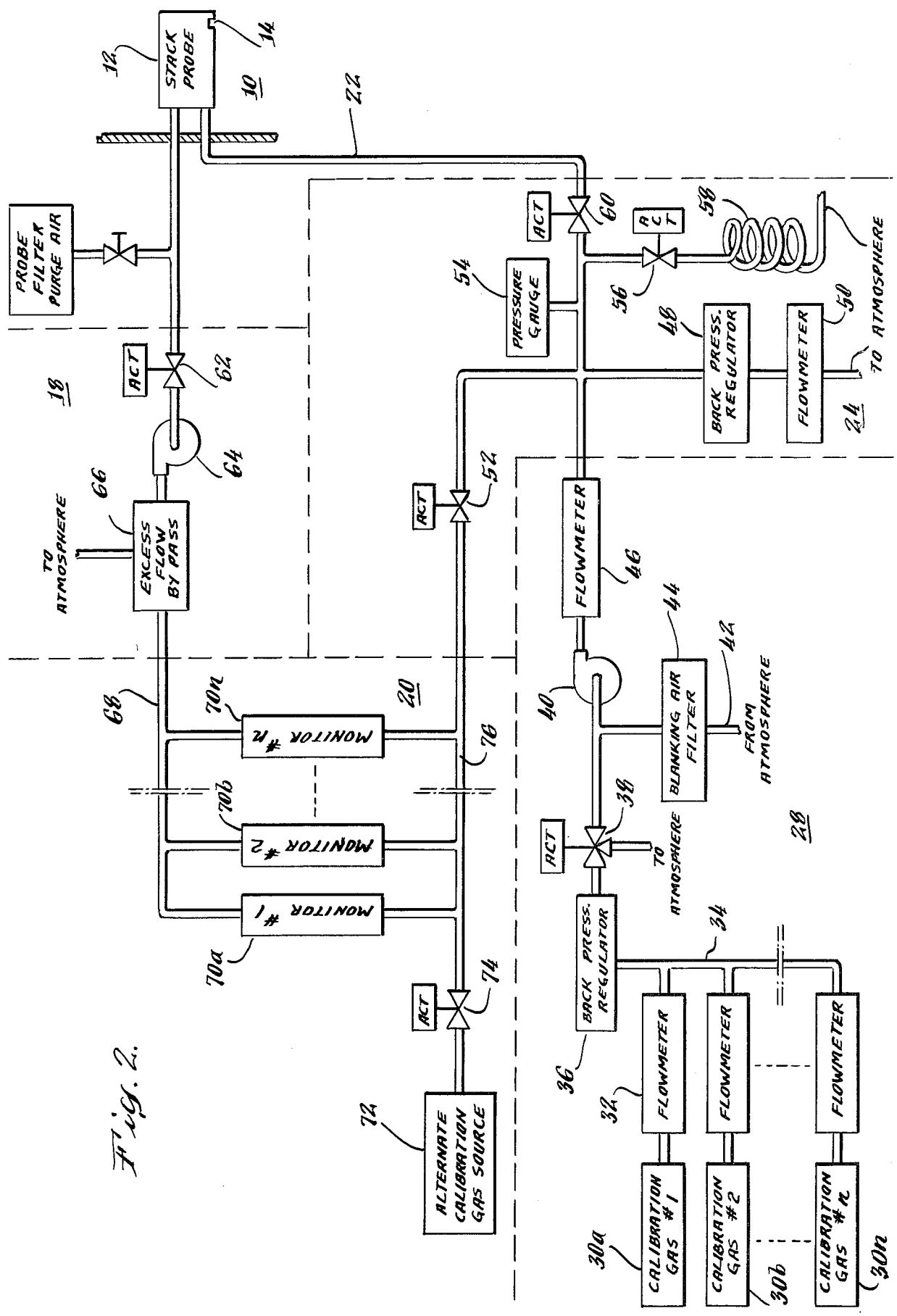
FIG. 2 is a more detailed block diagram of the analyzer system shown in FIG. 1.

Referring to FIG. 2, most of the components shown very generally in FIG. 1, are illustrated in more detail.

For example, in a preferred embodiment of the invention, calibration gases and blanking air generator 28 includes sources 30a, 30b...30n of known concentrations of suspected constituents in the stack gas flow. As an example, source 30a may be a cylinder of concentrated hydrogen sulfide gas while source 30b might be a similar cylinder of sulphur dioxide gas. The output of each calibration gas source is connected through a flowmeter, such as flowmeter 32 to a manifold 34 having a single output to a back pressure regulator 36. The back pressure regulator 36 establishes a constant pressure on the output side of the flowmeter which permits adjustments to be made in the concentration of individual calibration gases without changing the concentrations of other gases introduced into the system. The back pressure regulator 36 is connected to a three-way valve 38 which, for reasons to be described later, can either vent the calibration gases to the exterior of the system or cause those gases to be supplied to the inlet side of a pump 40. Blanking air is introduced into the system through a second connection at the input of pump 40. The second connection includes an inlet 42 from the atmosphere and a blanking air filter 44 which may be of any suitable construction for the removal of contaminants from the air entering through connection 42.

Pump 40, in combination with a flowmeter 46 in its outlet line, establishes a high rate of flow for the calibration gases and blanking air introduced to the flow control system 24. One branch of the flow control system 24 includes a back pressure regulator 48 in series with a flowmeter 50 for establishing a fixed pressure drop between the outlet side of the flowmeter 46 and atmosphere. Flow control system 24 further includes a valve 52 which can be used to establish a direct connection between the outlet side of flowmeter 46 and the gas analyzers 20. A pressure gauge 54 permits the pressure on the output side of flowmeter 46 to be monitored. The system 24 also has a valve 56 leading to a tubing coil 58 and another valve 60 communicating with probe 12. Valve 56 and the tubing coil 58 can be used to establish a variable pressure drop which matches the pressure drop which would occur from valve 60 along inlet line 22 to the second inlet of probe 12. Outlet 16 of probe 12 is connected to a valve 62 in line between the outlets 16 and the inlet of another pump 64 in the high volume sample delivery system. When the valve 62 is open and the pump 64 is operating, pump 64 causes the contents of the probe 12 to be transferred toward the analyzers 20 at a rate greater than the rate of which the analyzers can accept the flow. The excess flow is vented to the exterior of the system through an excess flow bypass 66, which preferably communicates with stack 10 downstream of probe 12. A manifold 68 connects the common output from the bypass 66 to the individual gas analyzers 70a, 70b,...70n, each of which is designed to monitor specific constituents in the stack gas. Neither the details of the analyzers nor the means for obtaining information from the analyzers are shown as these are not considered to be a critical part of the present invention.

In an alternate mode of operation, calibration gases may be supplied directly to the analyzers 70a, 70b, etc. from an alternate calibration gas source 72 isolated from the analyzers 20 by a valve 74. The source 72 can be used as a back up source in the event of some failure in the operation of generator 28 or flow control system 24. Source 72 can also be used to calibrate the analyzers so that the analyzers can provide a check on the concentration of calibrating gases being provided by the generator 28.

The rates of flow which are established in various parts of the system are important to the proper operation of the system. The rate of flow on the upstream side of valve 52 exceeds the rate of flow on the downstream side of the excess flow bypass 66 so that calibrating gases supplied through valve 52 can flood the analyzers 70a, 70b, etc. even when pump 64 is operating. The stack gas which is forced from the analyzers by the directly-supplied calibrating gases is vented to the exterior of the system through the excess flow bypass 66. Similarly, the rate of flow at the output of valve 60, which is the input 22 to probe 12, exceeds the rate of flow established by the pump 64 when valve 56 is closed. Thus when valve 56 is closed and valve 60 is open, calibrating gases applied to the input of the stack probe 12 will flood the probe preventing stack gases from entering the probe through inlet 14. The high volume sample delivery system 18, while continuing to pump, will actually be sampling only calibrating gases under these conditions.

The system described in FIG. 2 operates in a number of different modes. A brief description of each of those modes of operations follows.

During normal stack sampling operations, vales 62 and 56 are open while valve 60 is closed. Valve 38 may be set to direct calibration gases either to the inlet pump 40 or to atmosphere. Under these conditions, the calibrating gases supplied by the sources 30a, 30b, etc., are vented to atmosphere either at valve 38 or through valve 56 and tubing coil 58. Since the tubing coil can be adjusted to provide a pressure drop equal to that occurring between the valve 60 and the probe 12, the line pressure and the rate of flow of calibration gases in the system can be maintained within the flow control system 24 at the same levels as exist when valve 60 is open. But with valve 60 closed, stack gases enter the probe 12 through inlet 14 and are transferred through valve 62, pump 64 and excess flow bypass 66 to the manifold 68 at the upper end of the analyzers 70a, 70b, etc. Of course, the pump 64 provides more stack gas than can be used by the analyzers with the excess being vented at the bypass 66.

It is possible to provide blanking air to the entire system by operating valves 56, 60 and 62 while venting calibration gases from sources 30a, 30b, etc. to atmosphere at the three-way valve 38. Under these conditions, blanking air provided through filter 44 at the input to pump 40 is delivered to the inlet 22 of probe 12 to flood the probe and force out stack gases. The high volume delivery system 18 then provides a part of the blanking gas to the manifold 68 leading to the analyzers.

In a normal calibration mode, valves 62 and 60 are open while calibration gases are provided at the input to pump 40 by the three-way valve 38. The calibration gases, after flooding the interior of the probe 12, are conveyed to the manifold 68 by high volume delivery system 18.

It is also possible to blank the analyzers directly without using the high volume sample delivery system. Valve 62 remains open while either valve 60 or 56 is opened. Valve 52 is also open while calibration gases are vented to atmosphere at the three-way valve 38. Under these conditions, blanking air from the filter 44 is provided at the inlet side of the valves 52 and 56. By properly selecting the rate of flow at this point, the blanking air delivered directly to the analyzers 70a, 70b, etc. can, notwithstanding the pressure loss through valve 56 or valve 60 (whichever is open) be great enough to flood the analyzers driving stack gases from the system at bypass 66.

Of course, it is also possible to calibrate the monitors directly from the generator 28 without using any part of the high volume sampling system. The valve arrangement is the same as when the monitors are directly blanked except that calibrating gases are delivered to the input of pump 40 by three-way valve 38 rather than being vented to atmosphere. Under these conditions, the calibrating gases travel through pump 40, flowmeter 46 and valve 52 to the manifold 76 at a rate of flow which is great enough to flood the analyzers, forcing stack gas to be vented to the exterior of the system at the bypass 66.

Thus, it will be seen that this system is capable of providing calibrating gases or blanking air to the analyzers either directly or along the entire path travelled by sample stack gases. Since the number of analyzers are supplied from the same sample delivery and calibrating system, the cost of installing and maintaining the entire system can be expected to be lower than the cost of installing the same number of analyzers each having its own sampling and/or calibrating system.

Figure 3:
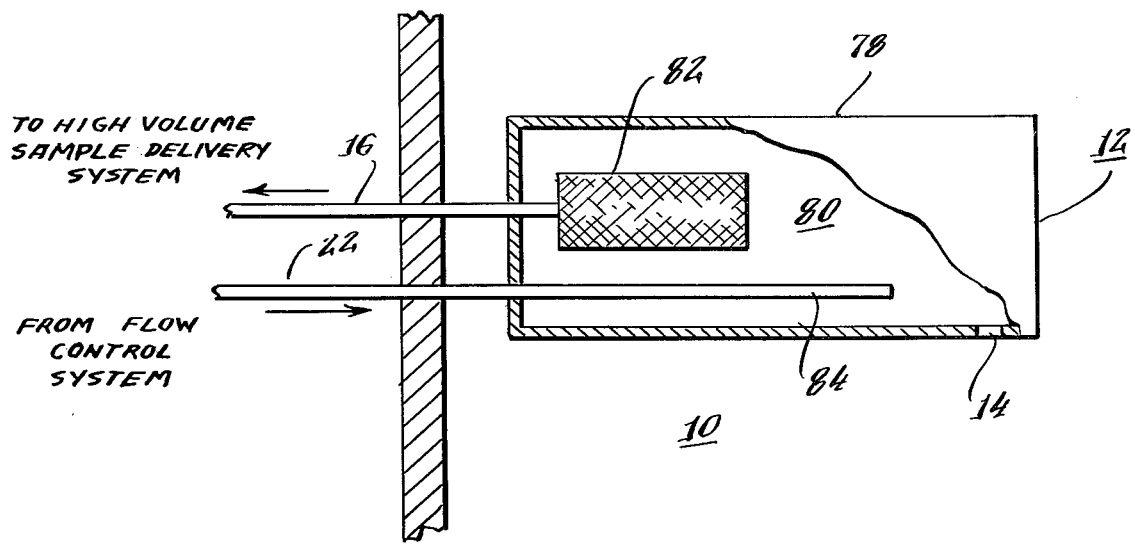
FIG. 3 is a partially cut away view of one embodiment of the sample probe for use with the present invention.

Referring now to FIG. 3, one embodiment of a stack probe suitable for use in the present invention includes a housing 78 having an inlet 14 from the stack 10 in which the housing is located. The housing 78 includes an interior chamber 80 which may contain a filter member 82 and an extension 84 of the inlet 22. The filter 82 is connected to the outlet 16 leading to the high volume sample delivery system.

When calibrating gases or blanking air are supplied through extension 84 to chamber 80, these gases flood chamber 80 preventing stack gases from entering at inlet 14. Filter 82 draws the calibrating gases or blanking air, as the case may be, to the high volume sample delivery system. When neither calibrating gas nor blanking air is supplied to the probe, the interior chamber 80 is filled with stack gases entering through the inlet 14.

Figure 4:
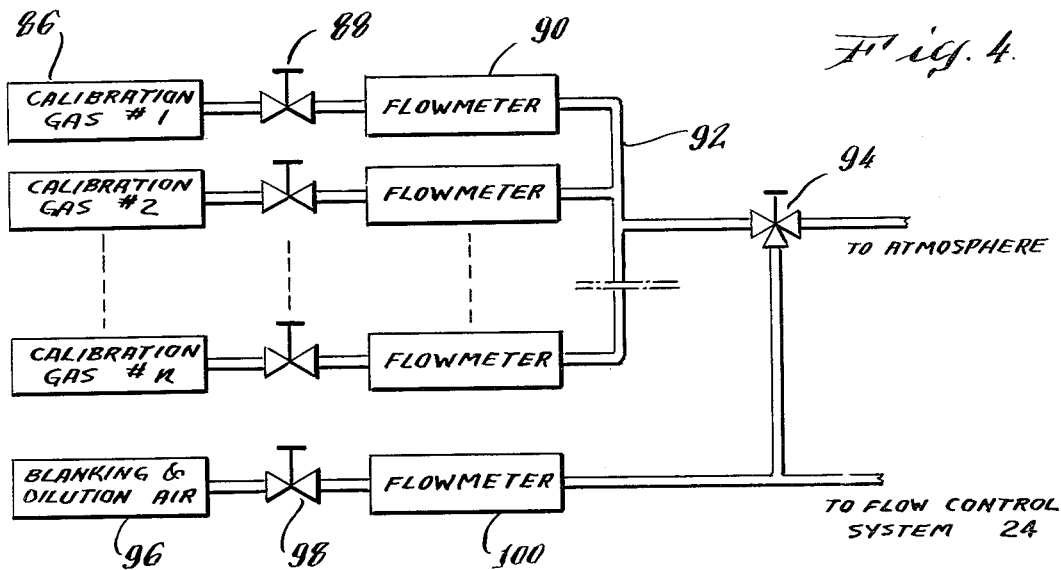
FIG. 4 is a block diagram of an alternate embodiment of a calibration gas and blank air generator for use in the system incorporating the present invention.

While the gas and air generator 28 described in detail in reference to FIG. 2 represents a preferred embodiment of the invention, other generator systems may also be used. FIG. 4 shows one such system. In this system each source of calibration gas is connected through a valve and flowmeter to a common manifold in which the calibration gases are combined. For example, calibration gas source 86 is connected through a valve 88 and a flowmeter 90 to a common output manifold 92. The combined calibration gases are applied to a three-way valve 94 which may either vent the calibration gases or apply them to the output side of a blanking and dilution air subsystem including a source 96, a valve 98 and a flowmeter 100.

This generator is somewhat less flexible than the generator described with reference to FIG. 2. If the flow of any calibration gas changes, the concentration of all other calibrating gases at the outlet of the generator will also change and must be redetermined.

Figure 5:
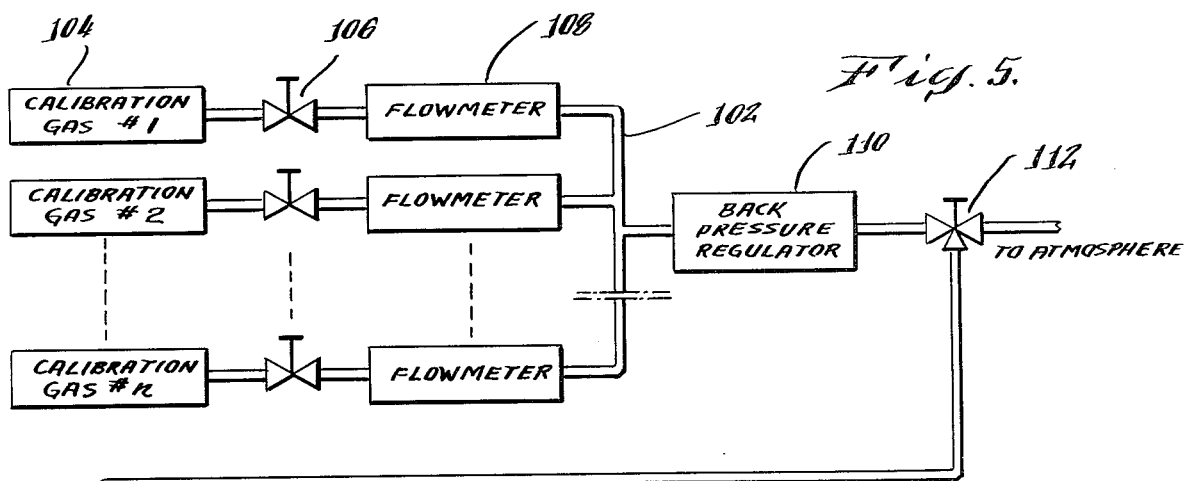
FIG. 5 is a block diagram of another alternate embodiment of a calibration gas and blank air generator for use in the system incorporating the present invention.
Figure 5:
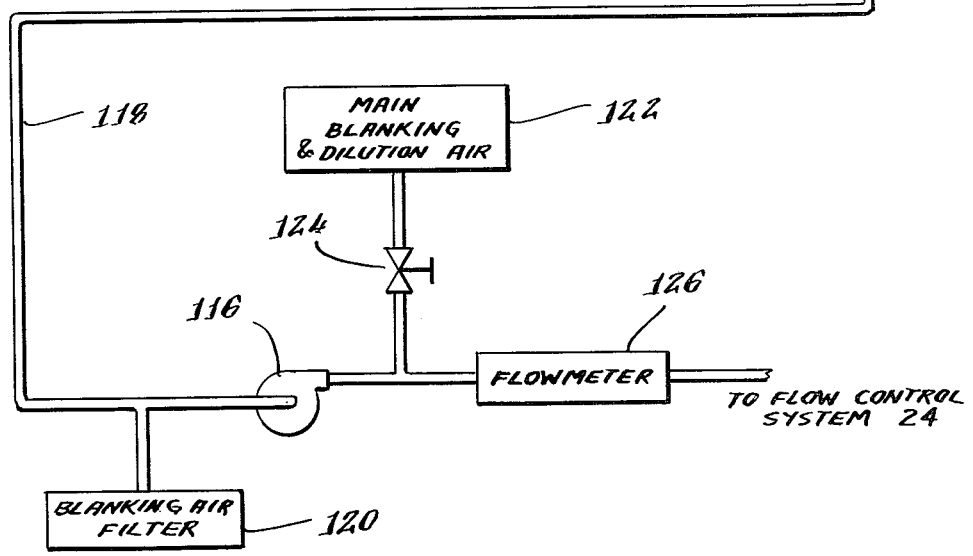

Another embodiment of a calibrating gases and blanking generator is shown in detail in FIG. 5. As in the system just described, each source of calibrating gas is connected through a valve and flowmeter to a common output manifold. For example, output manifold 102 receives a calibrating gas from a source 104 through a valve 106 and flowmeter 108. The combined flow in manifold 102 is applied to a back pressure regulator 110 which produces a constant pressure flow at an inlet to a three-way valve 112. Valve 112 can vent the combined calibrating gas flow or apply it to the inlet side of a pump 116 through a pipe 118. A blanking air filter 120 is connected to the inlet side of pump 116 at manifold 118 to provide a limited amount of blanking air. A main blanking and dilution air source 122 is connected to the outlet side of pump 116 through a valve 124. The combined flows from pump 116 and source 122 are directed through a flowmeter 126 to the flow control system.

In this generator, the total volume of generated gases is made from two sources. The major part of the generated gases is furnished by the source 122 while the minor part is provided through pump 116. Pump 116, which draws from both the blanking air filter 120 and the valve 112, furnishes a constant flow whether or not the calibration gases are entering conduit 118, permitting the entire generator to remain in a stand-by operating condition. The amounts of individual calibration gases which are supplied can be adjusted at any time without affecting the delivered concentration of other calibrating gases.

While there have been described what are considered to be preferred embodiments of the present invention, variations and modifications of the invention will occur to those skilled in the art once they become aware of the basic concepts of the invention. For example, a back pressure regulator might be used on the outlet side of the flowmeter 46 in the system shown in FIG. 2 to establish a constant pressure flow. A back pressure regulator at this location would eliminate the need for back pressure regulator 48 and flowmeter 50. Therefore, it is intended that the appended claims shall be construed as including not only the preferred embodiments but also all such variations and modifications as fall within the true spirit and scope of the invention.

What is claimed is:

1. For use in an effluent analyzing system having one or more analyzers for detecting the levels of suspected constituents, a calibration/sampling system including:

a. a chambered probe including a first inlet for receiving effluent samples, a second inlet and an outlet;
b. sample delivery means connected to the outlet for transferring the contents of said chambered probe to the analyzers at a predetermined rate of flow;
c. a calibrating fluid supply connected to the second inlet for selectively supplying known concentrations of fluids at a rate of flow greater than the rate established by said sample delivery means to force effluent from the chambered probe thereby permitting the analyzers to selectively receive calibrating fluid samples through the probe to the exclusion of effluent fluid samples.

2. A system as recited in claim 1 further including means for selectively supplying the calibrating fluids directly to the analyzers, bypassing the chambered probe and sample delivery system.

3. A system as recited in claim 1 further including means for maintaining said calibration means in a standby condition during effluent sampling, said standby maintaining means including valve means for causing the calibrating fluids to be selectively vented from the system.

4. A system as recited in claim 1 wherein said calibrating means includes a blanking fluid supply including:
a. a valve for selectively interrupting the flow of calibrating fluids;
b. a source of blanking fluid connected to said calibrating means at a point between said valve and said second inlet to said chambered probe.

5. A system as recited in claim 1 wherein said sample delivery means includes:
a. a pump for transferring the contents of said chambered probe at a rate of flow greater than the rate at which the contents can be accepted by the analyzers; and
b. a vent for exhausting the excess contents from the system.

6. A system as recited in claim 2 wherein the system has a first inlet to the analyzers from the sample delivery means and a second inlet from the means for directly supplying the calibrating fluids.

7. A system as recited in claim 3 wherein the calibrating fluids are supplied directly to the second inlet to the analyzers at a rate of flow exceeding the rate of flow at which contents of the chambered probe are transferred to the first input to the analyzers, whereby the analyzers can be selectively flooded with calibrating fluids without terminating the flow of contents of the chambered probe into the sample delivery means.

8. A system as recited in claim 1 wherein said calibrating fluid supply includes:
a. an outlet pump; and
b. flow regulating means connected to the outlet side of said pump for maintaining a desired rate of flow.

9. A system as recited in claim 1 further including an alternate supply of calibrating fluids which may be selectively connected directly to the analyzers, bypassing the sample delivery means and the calibrating means.

10. For use in a stack gas analyzing system having one or more analyzers for detecting suspected constituents in a stack gas flow, a calibration/sampling system including:
a. a chambered probe including a first inlet for receiving stack gas samples, a second inlet and an outlet;
b. a sample delivery subsystem connected to the outlet of said chambered probe for delivering samples to the analyzers at a predetermined rate of flow;
c. a calibrating gases supply subsystem connected to the second inlet of said chambered probe for selectively supplying calibrating gases at a rate of flow greater than the rate established within said sample delivery subsystem to force stack gases from the chambered probe, thereby permitting the analyzers to selectively receive calibrating gases through the probe to the exclusion of stack gases.

11. A system as recited in claim 10 further including means for selectively supplying calibrating gases directly to the analyzers, bypassing the chambered probe and sample delivery subsystem.

12. A system as recited in claim 10 further including means for maintaining said calibrating gases supply subsystem in a standby condition during stack gas sampling, said standby maintaining means including a valve for selectively venting calibrating gases externally of the system.

13. A system as recited in claim 10 wherein said calibrating gases supply subsystem includes a blanking air supply comprising:
a. a valve for selectively interrupting the introduction of calibrating gases into the system;
b. a connection to the exterior of the system for permitting air to be introduced into said calibrating gases supply subsystem at a point between said valve and the second inlet to said chambered probe; and
c. a filter in line in said connection for removing impurities in the air to be introduced into the system.

14. A system as recited in claim 10 wherein said sample delivery subsystem includes:
a. a pump for transferring the contents of said chambered probe at a rate of flow greater than the rate at which the contents can be accepted by the analyzers; and
b. a vent connected to said subsystem at a point between the analyzers and said pump for exhauting system gases in excess of those accepted by the analyzers.

15. A system as recited in claim 11 wherein the system has a first inlet to the analyzers from the sample delivery subsystem and a second inlet from the means for supplying calibrating gases directly.

16. A system as recited in claim 15 wherein the calibrating gases may be supplied directly to the second inlet to the analyzers at a rate of flow exceeding the rate of flow established at the first inlet by the sample delivery subsystem, whereby the analyzers can be selectively flooded with calibrating gases without terminating the flow of stack gas into the sample delivery subsystem.

17. A system as recited in claim 10 wherein said calibrating gases supply subsystem includes:
a. a pump; and
b. flow regulating means in line with the outlet from said pump for maintaining the rate of flow at a desired level.

18. A system as recited in claim 10 further including an alternate supply of calibrating gases which may be selectively connected directly to the analyzers, bypassing the sample delivery subsystem and the calibrating gases supply subsystem.

19. A system as recited in claim 12 wherein said calibrating gases supply subsystem includes a blanking air supply comprising:
   a. a valve for selectively interrupting the introduction of calibrating gases into the system;
   b. a connection to the exterior of the system for permitting air to be introduced into said calibrating gases supply subsystem at a point between said valve and the second inlet to said chambered probe; and
   c. a filter in line in said connection for removing impurities in the air to be introduced into the system.

20. A system as recited in claim 12 wherein said sample delivery subsystem includes:
   a. a pump for transferring the contents of said chambered probe at a rate of flow greater than the rate at which the contents can be accepted by the analyzers; and
   b. a vent connected to said subsystem at a point between the analyzers and said pump for exhausting system gases in excess of those accepted by the analyzers.

21. A system as recited in claim 12 wherein the calibrating gases may be supplied directly to the second inlet to the analyzers at a rate of flow exceeding the rate of flow established at the first inlet by the sample delivery subsystem, whereby the analyzers can be selectively flooded with calibrating gases without terminating the flow of stack gas into the sample delivery subsystem.

22. A system as recited in claim 19 wherein said sample delivery subsystem includes:
   a. a pump for transferring the contents of said chambered probe at a rate of flow greater than the rate at which the contents can be accepted by the analyzers; and
   b. a vent connected to said subsystem at a point between the analyzers and said pump for exhausting system gases in excess of those accepted by the analyzers.

23. A system as recited in claim 22 wherein the calibrating gases may be supplied directly to the second inlet to the analyzers at a rate of flow exceeding the rate of flow established at the first inlet by the sample delivery subsystem, whereby the analyzers can be selectively flooded with calibrating gases without terminating the flow of stack gas into the sample delivery subsystem.

* * * * *